US010214756B2

(12) United States Patent
Kondo et al.

(10) Patent No.: US 10,214,756 B2
(45) Date of Patent: Feb. 26, 2019

(54) METHOD FOR GENERATING OIL/FAT COMPONENT FROM CHLAMYDOMONAS ALGAE

(71) Applicants: National University Corporation Kobe University, Kobe-Shi (JP); Inter-University Research Institute Corporation National Institutes of Natural Sciences, Mitaka-shi, Tokyo (JP); DIC Corporation, Tokyo (JP)

(72) Inventors: Akihiko Kondo, Kobe (JP); Tomohisa Hasunuma, Kobe (JP); Shih-hsin Ho, Kobe (JP); Jun Minagawa, Okazaki (JP); Haruo Nishie, Sakura (JP); Hiroyuki Taroda, Sakura (JP); Jo-Shu Chang, Taichung (TW)

(73) Assignees: National University Corporation KOBE University, Kobe-shi (JP); Inter-University Research Institute Corporation National Institutes of Natural Sciences, Tokyo (JP); DIC Corporation, Tokyo (JP)

( * ) Notice: Subject to any disclaimer, the term of this patent is extended or adjusted under 35 U.S.C. 154(b) by 0 days.

(21) Appl. No.: 14/913,594

(22) PCT Filed: Mar. 17, 2014

(86) PCT No.: PCT/JP2014/057185
§ 371 (c)(1),
(2) Date: Feb. 22, 2016

(87) PCT Pub. No.: WO2015/025553
PCT Pub. Date: Feb. 26, 2015

(65) Prior Publication Data
US 2016/0201098 A1    Jul. 14, 2016

(30) Foreign Application Priority Data

Aug. 23, 2013   (JP) ................................ 2013-173417

(51) Int. Cl.
C12P 7/64    (2006.01)

(52) U.S. Cl.
CPC ............... *C12P 7/6409* (2013.01); *C12P 7/64* (2013.01); *C12P 7/6463* (2013.01); *C12P 7/649* (2013.01)

(58) Field of Classification Search
None
See application file for complete search history.

(56) References Cited

U.S. PATENT DOCUMENTS

2016/0201098 A1*   7/2016 Kondo .................. C12P 7/6463
                                                          435/134

FOREIGN PATENT DOCUMENTS

| JP | 07-075557   A  | 3/1995  |
|----|----------------|---------|
| JP | 11-196885   A  | 7/1999  |
| JP | 2000-316593 A  | 11/2000 |
| JP |    3837589 B2  | 10/2006 |
| JP |    4081794 B2  | 4/2008  |
| JP | 2009-060876 A  | 3/2009  |
| JP | 2013-102748 A  | 5/2013  |

OTHER PUBLICATIONS

M.Takagi et al., "Effect of Salt Concentration on Intracellular Accumulation of Lipids and Triacylglyceride in Marine Microalgae *Dunaliella* Cells," Journal of Bioscience and Bioengineering,vol. 101, 2006, pp. 223-226.
Y. Collos et al., "An optical method for the rapid measurement of micromolar concentrations of nitrate in marine phytoplankton cultures," Journal of Applied Phycology,vol. 11, 1999, pp. 179-184.
M.Siaut et al., "Oil accumulation in the model green alga *Chlamydomonas reinhardtii*: characterization, variability between common laboratory strains and relationship with starch reserves," BMC Biotechnology, vol. 11, No. 7, 2011, pp. 1-15.
A. R. Rao et al., "Effect of salinity on growth of green alga *Botryococcus braunii* and its constituents," Bioresource Technology, vol. 98, 2007, pp. 560-564.
A. Nakanishi et al., "Development of high lipid producing system by green alga *Chlamydomonas orbicularis* under sea salt condition," Abstracts of the Annual meeting of the society for Biotechnology, Japan, vol. 65, Aug. 25, 2013, p. 64 (1P-185).
E. S. Salama et al., "Biomass, lipid content, and fatty acid composition of freshwater *Chlamydomonas mexicana* and *Scenedesmus obliquus* grown under salt stress," Bioprocess Biosyst. Eng, vol. 36, 2013, pp. 827-833.
S.-H. Ho et al., "Phototrophic cultivation of a marine microalga *Chlamydomonas orbicularis* for $CO_2$ fixation and biodiesel production: Effect of medium composition, nitrogen depletion, and sea salt concentration," Abstracts of the Annual meeting of the society for Biotechnology, Japan, vol. 65, Aug. 25, 2013, p. 66 (1P-196).
A. Nakanishi et al., "Development of lipid productivities under different $CO_2$ conditions of marine microalgae *Chlamydomonas* sp. JSC4," Bioresource Technology, vol. 152, 2014, pp. 247-252.
International Search Report dated Apr. 28, 2014, issued for PCT/JP2014/057177 and English translation thereof.
International Search Report dated Jun. 17, 2014, issued for PCT/JP2014/057185 and English translation thereof.
Anonymous: "Sea salt", Wikipedia, the free encyclopedia, Aug. 13, 2013, XP002765650, Retrieved from the Internet: URL: <https://web.archive.org/web/20130813030057/http://en.wikipedia.org/wiki/Sea_Salt> [retrieved on Jan. 4, 2017] (cited in the Jan. 25, 2017 EP Search Report).
Greenbaum E et al: "Hydrogen and Oxygen Photo Production by Marine Algae", Photochemistry and Photobiology, vol. 37, No. 6, Jun. 1, 1983, pp. 649-656. (cited in the Jan. 25, 2017 EP Search Report).

(Continued)

*Primary Examiner* — Hope Robinson
(74) *Attorney, Agent, or Firm* — Locke Lord LLP; James E. Armstrong, IV; Nicholas J. DiCeglie, Jr.

(57) ABSTRACT

There is provided a method for generating an oil/fat component by means of culturing algae, in which marine algae belonging to *chlamydomonas* are cultured in a culture medium containing sea salt.

14 Claims, 7 Drawing Sheets

Specification includes a Sequence Listing.

(56) References Cited

OTHER PUBLICATIONS

Search Report dated Jan. 25, 2017, issued for the European Patent Application No. 14838058.7.
Supplementary European Search Report dated Mar. 17, 2017, issued for the European patent application No. 14837252.7.
Shih-Hsin Ho et al., "Optimizing biodiesel production in marine *Chlamydomonas* sp. JSC4 through metabolic profiling and an innovative salinity-gradient strategy," Biotechnology for Biofuels, Biomed Central Ltd, GB, vol. 7, No. 1, Jun. 24, 2014, p. 97 (16 pages).
Office Action issued in co-pending U.S. Appl. No. 14/913,618, dated Sep. 18, 2017.
R. H. Al-Hasan et al., "Correlative Changes of Growth, Pigmentation and Lipid Composition of Dunaliella salina in Response to Halostress", Journal of General Microbiology 133, 2607-2616, (1987).
N. Lu et al., "Regulation of lipid metabolism in the snow alga *Chlamydomonas nivalis* in response to NaCl stress; An integrated analysis by cytomic and lipidomic approaches," Process Biochemistry 47, 1163-1170, (2012).
Office Action issued for corresponding European Patent Application No. 14 838 058.7, dated Mar. 1, 2018.
An Meiling et al: "Expression of fatty acid desaturase genes and fatty acid accumulation in *Chlamydomonas* sp. ICE-L under salt stress", Bioresource Technology, vol. 149, pp. 77-83, (2013).
N. Lu et al., "Regulation of lipid metabolism in the snow alga *Chlamydomonas nivalis* in response to NaC1 stress; An integrated analysis by cytomic and lipidomic approaches," Process Biochemistry 47, 1163-1170, (2012).

\* cited by examiner

FIG. 2

```
                                                  1                                                    50
[SEQ. ID:1]    Chlamydomonas sp. JSC4         TAC-TTAGCA TGGAATAACA CGATAGGACT CTGGCCTATC T-GTTGGTCT
[SEQ. ID:2]    Chlamydomonas debaryana        TACATTAGCA TGGAATAACA CGATAGGACT CTGGCCTATC T-GTTGGTCT
[SEQ. ID:3]    Chlamydomonas cribrum          TACATTAGCA TGGAATAACA CGATAGGACT CTGGCCTATC T-GTTGGTCT
[SEQ. ID:4]    Chlamydomonas incerta          TACATTAGCA TGGAATAACA CGATAGGACT CTGGCCTATC T-GTTGGTCT
[SEQ. ID:5]    Chlamydomonas reinhardtii      TACATTAGCA TGGAATAACA CGATAGGACT CTGGCCTATC T-GTTGGTCT
[SEQ. ID:6]    Chlamydomonas zebra            TACATTAGCA TGGAATAACA CGATAGGACT CTGGCCTATC T-GTTGGTCT
[SEQ. ID:7]    Chlamydomonas oogama           TACATTAGCA TGGAATAACA CGATAGGACT CTGGCCTATC T-GTTGGTCT
[SEQ. ID:8]    Chlamydomonas longispicula     TACGTTAGCA TGGAATAACA TGATAGGACT CTGGCCTATC TTGTTGGTCT
[SEQ. ID:9]    Chlamydomonas pseudovolvox     TACATTAGCA TGGAATAACA CGATAGGACT CTGGCCTATC T-GTTGGTCT
[SEQ. ID:10]   Chlamydomonas sociale          TACATTAGCA TGGAATAACA TGATAGGACT CTGGCCTATC T-GTTGGTCT
[SEQ. ID:11]   Chlamydomonas carteri          TACATTAGCA TGGAATAACA CGATAGGACT CTGGCCTATC T-GTTGGTCT 51                                                   100
[SEQ. ID:1 cont.]    Chlamydomonas sp. JSC4         GTGGGACCGG AGTAATGATT AAGAGGGGTA GGCGGGGGCA TTCGTATCCC
[SEQ. ID:2 cont.]    Chlamydomonas debaryana        GTGGGACCGG AGTAATGATT AAGAGGGGTA GTCGGGGGCA TTCGTATTCC
[SEQ. ID:3 cont.]    Chlamydomonas cribrum          GTGGGACCGG AGTAATGATT AAGAGGGGTA GTCGGGGGCA TTCGTATTGC
[SEQ. ID:4 cont.]    Chlamydomonas incerta          GTGGGACCGG AGTAATGATT AAGAGGGGTA GTCGGGGGCA TTCGTATTCC
[SEQ. ID:5 cont.]    Chlamydomonas reinhardtii      GTGGGACCGG AGTAATGATT AAGAGGGGTA GTCGGGGGCA TTCGTATTCC
[SEQ. ID:6 cont.]    Chlamydomonas zebra            GTGGGACTGG AGTAATGATT AAGAGGGGTA GTCGGGGGCA TTCGTATTCC
[SEQ. ID:7 cont.]    Chlamydomonas oogama           GTGGGACCGG AGTAATGATT AAGAGGGGTA GTCGGGGGCA TTCGTATTCC
[SEQ. ID:8 cont.]    Chlamydomonas longispicula     GTAGGACTGG AGTAATGATT AAGAGGGACA GTCGGGGGCA TTCGTATTGC
[SEQ. ID:9 cont.]    Chlamydomonas pseudovolvox     GTGGGACCGG AGTAATGATT AAGAGGGACA GTCGGGGGCA TTCGTATTCC
[SEQ. ID:10 cont.]   Chlamydomonas sociale          GTGGGACCGG AGTAATGATT AAGAGGGGTA GTCGGGGGCA TTCGTATTCC
[SEQ. ID:11 cont.]   Chlamydomonas carteri          GTGGGATCGG AGTAATGATT AAGAGGGGTA GTCGGGGGCA TTCGTATTCC 101                                                  150
[SEQ. ID:1 cont.]    Chlamydomonas sp. JSC4         GTTGTCAGAG GTGAGATTCT TGGATGTACG GAAGACAAAC ATCTGCGAAA
[SEQ. ID:2 cont.]    Chlamydomonas debaryana        GTTGTCAGAG GTGAAATTCT TGGATTTACG GAAGACGAAC ATNTGCGAAA
[SEQ. ID:3 cont.]    Chlamydomonas cribrum          GTTGTCAGAG GTGAAATTCT TGGATTTACG CAAGACGAAC ATCTGCGAAA
[SEQ. ID:4 cont.]    Chlamydomonas incerta          GTTGTCAGAG GTGAAATTCT TGGATTTACG GAAGACGAAC ATCTGCGAAA
[SEQ. ID:5 cont.]    Chlamydomonas reinhardtii      GTTGTCAGAG GTGAAATTCT TGGATTTACG GAAGACGAAC ATCTGCGAAA
[SEQ. ID:6 cont.]    Chlamydomonas zebra            GTTGTCAGAG GTGAAATTCT TGGATTTACG GAAGACGAAC ATCTGCGAAA
[SEQ. ID:7 cont.]    Chlamydomonas oogama           GTTGTCAGAG GTGAAATTCT TGGATTTACG GAAGACGAAC ATCTGCGAAA
[SEQ. ID:8 cont.]    Chlamydomonas longispicula     GCTGTCAGAG GTGAAATTCT TGGATTTGCG CAAGACGAAC ATCTGCGAAA
[SEQ. ID:9 cont.]    Chlamydomonas pseudovolvox     ATTGTCAGAG GTGAAATTCT TGGATTTATG GAAGACGAAC ATCTGCGAAA
[SEQ. ID:10 cont.]   Chlamydomonas sociale          GTTGTCAGAG GTGAAATTCT TGGATTTACG GAAGACGAAC ATCTGCGAAA
[SEQ. ID:11 cont.]   Chlamydomonas carteri          GTTGTCAGAG GTGAAATTCT TGGATTTACG GAAGACGAAC ATCTGCGAAA 151                                                  200
[SEQ. ID:1 cont.]    Chlamydomonas sp. JSC4         GCATTTGCCA AGGATACTTT CATTGATCAA G-----GGGT TGGGGGCTTG
[SEQ. ID:2 cont.]    Chlamydomonas debaryana        GCATTTGCCA AGGATACTTT CATTGATCAA GAACGAAAGT TGGGGGCTCG
[SEQ. ID:3 cont.]    Chlamydomonas cribrum          GCATTTGCCA AGGATACTTT CATTGATCAA GAACGAAAGT TGGGGGCTCG
[SEQ. ID:4 cont.]    Chlamydomonas incerta          GCATTTGCCA AGGATACTTT CATTGATCAA GAACGAAAGT TGGGGGCTCG
[SEQ. ID:5 cont.]    Chlamydomonas reinhardtii      GCATTTGCCA AGGATACTTT CATTGATCAA GAACGAAAGT TGGGGGCTCG
[SEQ. ID:6 cont.]    Chlamydomonas zebra            GCATTTGCCA AGGATACTTT CATTGATCAA GAACGAAAGT TGGGGGCTCG
[SEQ. ID:7 cont.]    Chlamydomonas oogama           NCATTTGCCA AGGATACTTT CATTGATCAA GAACGAAAGT TGGGGGCTCG
[SEQ. ID:8 cont.]    Chlamydomonas longispicula     GCATTTGCCA AGGATGTTTT CATTGATCAA GAACGAAAGT TGGGGGCTCG
[SEQ. ID:9 cont.]    Chlamydomonas pseudovolvox     GCATTTGCCA AGGATGTTTC -ATTGATCAA GAACGAAAGT TGGGGGCTCG
[SEQ. ID:10 cont.]   Chlamydomonas sociale          GCATTTGCCA AGGATACTTT CATTGATCAA GAACGAAAGT TGGGGGCTCG
[SEQ. ID:11 cont.]   Chlamydomonas carteri          GCATTTGCCA AGGATACTTT CATTGATCAA GAACGAAAGT TGGGGGCTCG
```

FIG. 3

```
                                                   201                                                    250
[SEQ. ID:1 cont.]   Chlamydomonas sp. JSC4         AAGACGGTTA GATACCGTCG TAGTCTCAAC CATAAACGAT GCCGACTAGG
[SEQ. ID:2 cont.]   Chlamydomonas debaryana        AAGACGATTA GATACCGTCG TAGTCTCAAC CATAAACGAT GCCGACTAGG
[SEQ. ID:3 cont.]   Chlamydomonas cribrum          AAGACGATTA GATACCGTCG TAGTCTCAAC CATAAACGAT GCCGACTAGG
[SEQ. ID:4 cont.]   Chlamydomonas incerta          AAGACGATTA GATACCGTCG TAGTCTCAAC CATAAACGAT GCCGACTAGG
[SEQ. ID:5 cont.]   Chlamydomonas reinhardtii      AAGACGATTA GATACCGTCG TAGTCTCAAC CATAAACGAT GCCGACTAGG
[SEQ. ID:6 cont.]   Chlamydomonas zebra            AAGACGATTA GATACCGTCG TAGTCTCAAC CATAAACGAT GCCGACTAGG
[SEQ. ID:7 cont.]   Chlamydomonas oogama           AAGACGATTA GATACCGTCG TAGTCTCAAC CATAAACGAT GCCGACTAGG
[SEQ. ID:8 cont.]   Chlamydomonas longispicula     AAGACGATTA GATACCGTCG TAGTCTCAAC CATAAACGAT GCCGACTAGG
[SEQ. ID:9 cont.]   Chlamydomonas pseudovolvox     AAGACGATTA GATACCGTCG TAGTCTCAAC CATAAACGAT GCCGACTAGG
[SEQ. ID:10 cont.]  Chlamydomonas sociale          AAGACGATTA GATACCGTCG TAGTCTCAAC CATAAACGAT GCCGACTAGG
[SEQ. ID:11 cont.]  Chlamydomonas carteri          AAGACGATTA GATACCGTCG TAGTCTCAAC CATAAACGAT GCCGACTAGG 251                                                    300
[SEQ. ID:1 cont.]   Chlamydomonas sp. JSC4         GATTGGCAGA TGTTCCTTTG ATGACTCTGC CAGCACCTTA TAAGGAATCA
[SEQ. ID:2 cont.]   Chlamydomonas debaryana        GATTGGCAGA TGTTCCTTTG ATGACTCTGC CAGCACCTTA TGAGAAATCA
[SEQ. ID:3 cont.]   Chlamydomonas cribrum          GATTGGCGGG TGTTCCTTTG ATGACCCCGC CAGCACCTTA TGAGAAATCA
[SEQ. ID:4 cont.]   Chlamydomonas incerta          GATTGGCAGA TGTTCTTTTG ATGACTCTGC CAGCACCTTA TGAGAAATCA
[SEQ. ID:5 cont.]   Chlamydomonas reinhardtii      GATTGGCAGA TGTTCTTTTG ATGACTCTGC CAGCACCTTA TGAGAAATCA
[SEQ. ID:6 cont.]   Chlamydomonas zebra            GATTGGCGGA TGTTCTTTTG ATGACTCCGC CAGCACCTTA TGAGAAATCA
[SEQ. ID:7 cont.]   Chlamydomonas oogama           GATTGGCAGA TGTTCCTTTA ATGACTCTGC CAGCACCTTA TGAGAAATCA
[SEQ. ID:8 cont.]   Chlamydomonas longispicula     GATTGGTGGG AGTTTCTTCG ATGACTCCGC CAGCACCTTA TGAGAAATCA
[SEQ. ID:9 cont.]   Chlamydomonas pseudovolvox     GATTGGCAGA TGTTCCATTG ATGACTCTGC CAGCACCTTA TGAGAAATCA
[SEQ. ID:10 cont.]  Chlamydomonas sociale          GATTGGCAGA TGTTCCTTTG ATGACTCTGC CAGCACCTTA TGAGAAATCA
[SEQ. ID:11 cont.]  Chlamydomonas carteri          GATTGGCAGA TGTTCTTTTG ATGACTCTGC CAGCACCTTA TGAGAAATCA 301                                                    350
[SEQ. ID:1 cont.]   Chlamydomonas sp. JSC4         AAGTTTTTGG GTTCCGGGGG GAGTATGGTC ACAACGCTGA AACTTGAAGG
[SEQ. ID:2 cont.]   Chlamydomonas debaryana        AAGTTTTTGG GTTCCGGGGG GAGTATGGTC GCAAGGCTGA AACTTAAAGG
[SEQ. ID:3 cont.]   Chlamydomonas cribrum          AAGTTTTTGG GTTCCGGGGG GAGTATGGTC GCAAGGCTGA AACTTAAAGG
[SEQ. ID:4 cont.]   Chlamydomonas incerta          AAGTTTTTGG GTTCCGGGGG GAGTATGGTC GCAAGGCTGA AACTTAAAGG
[SEQ. ID:5 cont.]   Chlamydomonas reinhardtii      AAGTTTTTGG GTTCCGGGGG GAGTATGGTC GCAAGGCTGA AACTTAAAGG
[SEQ. ID:6 cont.]   Chlamydomonas zebra            AAGTTTTTGG GTTCCGGGGG GAGTATGGTC GCAAGGCTGA AACTTAAAGG
[SEQ. ID:7 cont.]   Chlamydomonas oogama           AAGTTTTTGG GTTCCGGGGG GAGTATGGTC GCAAGGCTGA AACTTAAAGG
[SEQ. ID:8 cont.]   Chlamydomonas longispicula     AAGTCTCTGG GTTCCGGGGG GAGTATGGTC GCAAGGCTGA AACTTAAAGG
[SEQ. ID:9 cont.]   Chlamydomonas pseudovolvox     AAGTTTTTGG GTTCCGGGGG GAGTATGGTC GCAAGGTTGA AACTTAAAGG
[SEQ. ID:10 cont.]  Chlamydomonas sociale          AAGTTTTTGG GTTCCGGGGG GAGTATGGTC GCAAGGCTGA AACTTAAAGG
[SEQ. ID:11 cont.]  Chlamydomonas carteri          AAGTTTTTGG GTTCCGGGGG GAGTATGGTC GCAAGGCTGA AACTTAAAGG 351                                                    400
[SEQ. ID:1 cont.]   Chlamydomonas sp. JSC4         AATTGACGGA AGGGCACCAC CAGGGCCACA AGCCTGCGGC TTAATTTGTC
[SEQ. ID:2 cont.]   Chlamydomonas debaryana        AATTGACGGA AGGGCACCAC CAGGCGTGG- AGCCTGCGGC TTAATTTGAC
[SEQ. ID:3 cont.]   Chlamydomonas cribrum          AATTGACGGA AGGGCACCAC CAGGCGTGG- AGCCTGCGGC TTAATTTGAC
[SEQ. ID:4 cont.]   Chlamydomonas incerta          AATTGACGGA AGGGCACCAC CAGGCGTGG- AGCCTGCGGC TTAATTTGAC
[SEQ. ID:5 cont.]   Chlamydomonas reinhardtii      AATTGACGGA AGGGCACCAC CAGGCGTGG- AGCCTGCGGC TTAATTTGAC
[SEQ. ID:6 cont.]   Chlamydomonas zebra            AATTGACGGA AGGGCACCAC CAGGCGTGG- AGCCTGCGGC TTAATTTGAC
[SEQ. ID:7 cont.]   Chlamydomonas oogama           AATTGACGGA AGGGCACCAC CAGGCGTGG- AGCCTGCGGC TTAATTTGAC
[SEQ. ID:8 cont.]   Chlamydomonas longispicula     AATTGACGGA AGGGCACCAC CAGGCGTGG- AGCCTGCGGC TTAATTTGAC
[SEQ. ID:9 cont.]   Chlamydomonas pseudovolvox     AATTGACGGA AGGGCACCAC CAGGCGTGG- AGCCTGCGGC TTAATTTGAC
[SEQ. ID:10 cont.]  Chlamydomonas sociale          AATTGACGGA AGGGCACCAC CAGGCGTGG- AGCCTGCGGC TTAATTTGAC
[SEQ. ID:11 cont.]  Chlamydomonas carteri          AATTGACGGA AGGGCACCAC CAGGCGTGG- AGCCTGCGGC TTAATTTGAC
```

FIG. 4

```
                                                       401                                                       450
[SEQ. ID:1 cont.]   Chlamydomonas sp. JSC4          TCAACACGGG GAAACTTACC AGGTCCAGAC ACGGGAAGGA TTGACAGATT
[SEQ. ID:2 cont.]   Chlamydomonas debaryana         TCAACACGGG GAAACTTACC AGGTCCAGAC ACGGGAAGGA TTGACAGATT
[SEQ. ID:3 cont.]   Chlamydomonas cribrum           TCAACACGGG GAAGCTTACC AGGTCCAGAC ACGGGAAGGA CTGACAGATT
[SEQ. ID:4 cont.]   Chlamydomonas incerta           TCAACACGGG GAAACTTACC AGGTCCAGAC ACGGGAAGGA TTGACAGATT
[SEQ. ID:5 cont.]   Chlamydomonas reinhardtii       TCAACACGGG GAAACTTACC AGGTCCAGAC ACGGGAAGGA TTGACAGATT
[SEQ. ID:6 cont.]   Chlamydomonas zebra             TCAACACGGG GAAACTTACC AGGTCCAGAC ACGGGAAGGA TTGACAGATT
[SEQ. ID:7 cont.]   Chlamydomonas oogama            TCAACACGGG GAAACTTACC AGGTCCAGAC ACGGGAAGGA TTGACAGATT
[SEQ. ID:8 cont.]   Chlamydomonas longispicula      TCAACACGGG AAAACTTACC AGGTCCAGAC ACAGGGAAGGA TTGACAGATT
[SEQ. ID:9 cont.]   Chlamydomonas pseudovolvox      TCAACACGGG GAAACTTACC AGGTCCAGAC ACGGGAAGGA TTGACAGATT
[SEQ. ID:10 cont.]  Chlamydomonas sociale           TCAACACGGG GAAACTTACC AGGTCCAGAC ACGGGAAGGA TTGACAGATT
[SEQ. ID:11 cont.]  Chlamydomonas carteri           TCAACACGGG GAAACTTACC AGGTCCAGAC ACGGGAAGGA TTGACAGATT 451                                                       500
[SEQ. ID:1 cont.]   Chlamydomonas sp. JSC4          GAGAGCTCTT TCTTAATTCT GTGGGTCGTG GTGCATGGCC GTTCTTAGTT
[SEQ. ID:2 cont.]   Chlamydomonas debaryana         GAGAGCTCTT TCTTGATTCT GTGGGTGGTG GTGCATGGCC GTTCTTAGTT
[SEQ. ID:3 cont.]   Chlamydomonas cribrum           GAGAGCTCTT TCTTGATTCT GTGGGTGGTG GTGCATGGCC GTTCTTAGTT
[SEQ. ID:4 cont.]   Chlamydomonas incerta           GAGAGCTCTT TCTTGATTCT GTGGGTGGTG GTGCATGGCC GTTCTTAGTT
[SEQ. ID:5 cont.]   Chlamydomonas reinhardtii       GAGAGCTCTT TCTTGATTCT GTGGGTGGTG GTGCATGGCC GTTCTTAGTT
[SEQ. ID:6 cont.]   Chlamydomonas zebra             GAGAGCTCTT TCTTGATTCT GTGGGTGGTG GTGCATGGCC GTTCTTAGTT
[SEQ. ID:7 cont.]   Chlamydomonas oogama            GAGAGCTCTT TCTTGATTCT GTGGGTGGTG GTGCATGGCC GTTCTTAGTT
[SEQ. ID:8 cont.]   Chlamydomonas longispicula      GAGAGCTCTT TCTTGATTCT GTGGGTGGTG GTGCATGGCC GTTCTTAGTT
[SEQ. ID:9 cont.]   Chlamydomonas pseudovolvox      GAGAGCTCTT TCTTGATTCT GTGGGTGGTG GTGCATGGCC GTTCTTAGTT
[SEQ. ID:10 cont.]  Chlamydomonas sociale           GAGAGCTCTT TCTTGATTCT GTGGGTGGTG GTGCATGGCC GTTCTTAGTT
[SEQ. ID:11 cont.]  Chlamydomonas carteri           GAGAGCTCTT TCTTGATTCT GTGGGTGGTG GTGCATGGCC GTTCTTAGTT 501
[SEQ. ID:1 cont.]   Chlamydomonas sp. JSC4          GG
[SEQ. ID:2 cont.]   Chlamydomonas debaryana         GG
[SEQ. ID:3 cont.]   Chlamydomonas cribrum           GG
[SEQ. ID:4 cont.]   Chlamydomonas incerta           GG
[SEQ. ID:5 cont.]   Chlamydomonas reinhardtii       GG
[SEQ. ID:6 cont.]   Chlamydomonas zebra             GG
[SEQ. ID:7 cont.]   Chlamydomonas oogama            GG
[SEQ. ID:8 cont.]   Chlamydomonas longispicula      GG
[SEQ. ID:9 cont.]   Chlamydomonas pseudovolvox      GG
[SEQ. ID:10 cont.]  Chlamydomonas sociale           GG
[SEQ. ID:11 cont.]  Chlamydomonas carteri           GG
```

|  | Fatty acid composition (%) | | |
|---|---|---|---|
|  | 2.0% sea salt condition | | SBO-based biodiesel |
|  | Nitrogen rich | Nitrogen depletion |  |
| Palmitic acid (C16:0) | 25.8 ± 0.6 | 27.6 ± 0.3 | 10.7 |
| Palmitoletic acid (C16:1) | 1.1 ± 0.0 | 3.2 ± 0.1 | 0 |
| Stearic acid (C18:0) | 4.0 ± 1.5 | 3.1 ± 0.1 | 4.4 |
| Oletic acid (C18:1) | 9.1 ± 0.0 | 26.6 ± 0.6 | 23.3 |
| Linoleic acid (C18:2) | 21.7 ± 0.0 | 25.3 ± 0.3 | 54.1 |
| Linolenic acid (C18:3) | 14.4 ± 0.4 | 5.4 ± 0.1 | 7.5 |
| Saturated fatty acid (SFA) | 28.3 ± 0.3 | 30.7 ± 0.5 | 15.1 |
| Monounsaturated fatty acid (MUFA) | 9.8 ± 0.4 | 29.7 ± 0.5 | 23.3 |
| Polyunsaturated fatty acid (PUFA) | 35.0 ± 0.9 | 30.7 ± 0.4 | 61.6 |
| C16 & C18 groups | 76.0 ± 0.5 | 91.1 ± 1.3 | 100 |

METHOD FOR GENERATING OIL/FAT COMPONENT FROM CHLAMYDOMONAS ALGAE

TECHNICAL FIELD

The present invention relates to a method for generating an oil/fat component which is useful as a fuel or a chemical raw material and particularly relates to a method for generating an oil/fat component, in which algae belonging to *Chlamydomonas* are cultured in a culture medium containing sea salt.

BACKGROUND ART

Photosynthetic organisms are used as a general term of organisms that fix $CO_2$ using light energy and particularly an alga indicates a kind of photosynthetic organism with high photosynthetic efficiency under excellent culture conditions. Since the industrial cultivation of algae has been performed for more than half a century and there has been a demand for algae to be used as industrial raw materials, fuels, feed and raw materials of fine chemicals, and health food, it is considered that the algae production occupies an important place in the future of industry.

Since various useful carbon components are generated through the process of fixation of $CO_2$, in the process of culturing algae, algae culture and the research on production of various carbon components through the culture have been actively conducted.

In the future, the need for early search for alternative fuels has been increased from the concern that fossil fuels are depleted and a demand for functional chemicals preferable for maintaining and improving health is increased due to an increase in health-oriented consumers. Therefore, there has been a growing interest in the useful components generated from algae.

In the related art, as an example of a method for producing a carbon component using algae, PTL 1 describes, as a production of ethanol useful for fuels or raw chemical materials, microalgae *Chlamydomonas* sp. MT-JE-SH-1 belonging to *Chlamydomonas* that produces ethanol from starch in cells by being grown at the salt concentration of seawater, accumulating starch in cells, and maintaining the cells under the dark and anaerobic atmosphere. As the means for solving the above-described problem, PTL 1 also describes a method for generating ethanol by culturing (1) microalgae *Chlamydomonas* sp. MT-JE-SH-1 belonging to *Chlamydomonas* that produces ethanol from starch in cells by being grown at the salt concentration of seawater, accumulating starch in cells, and maintaining the cells under the dark and anaerobic atmosphere and (2) microalgae *Chlamydomonas* sp. MT-JE-SH-1 belonging to *Chlamydomonas* at the salt concentration of seawater, accumulating starch in cells, and maintaining a slurry that contains the cultured alga body under the dark and anaerobic atmosphere while the pH thereof is maintained in a range of 6.0 to 9.0.

Further, as a method for producing an oil/fat component, PTL 2 describes a method for culturing a microorganism, that is, 4,7,10,13,16-docosapentaenoic acid-producing bacteria strain L59 (FERM P-18987) belonging to Labyrinthula in the Labyrinthulaceae, accumulating oils and fats containing 4,7,10,13,16-docosapentaenoic acid as a constituent fatty acid in bacterial cells, separating the bacterial cells, extracting the oils and fats from the separated bacterial cells using a solvent, and hydrolyzing the extract.

In NPL 1, the relation between generating oils and fats using marine algae and the salt concentration at the time of cultivation is examined and NPL 1 describes that the growth of algae is suppressed in a case where the initial concentration of the salt concentration exceeds 1.5 M and a high lipid content are generated in a case where the initial concentration thereof is in the range of 0.5 M to 1.0 M.

CITATION LIST

Patent Literature

[PTL 1] Japanese Patent No. 3837589
[PTL 2] Japanese Patent No. 4081794

Non-Patent Literature

[NPL 1] Journal of Bioscience and Bioengineering, Vol. 101, pp. 223 to 226 (2006)

SUMMARY OF INVENTION

Technical Problem

In the above-described background art, even though a useful carbon component is generated from algae, the carbon component has low production efficiency and does not fully meet the demands of customers. Therefore, provision of a method for generating a useful carbon component using algae with high production efficiency has been awaited.

Here, in consideration of the above-described background art, an object of the present invention is to provide a method for generating a useful carbon component with high efficiency using algae.

Solution to Problem

In order to solve the above-described problems, the present inventors conducted search for algae and intensive research on a method for culturing the algae, and solved the problem.

That is, in the present invention, the above-described problem is solved by means of providing a method for generating an oil/fat component described below, and new microalgae.

[1] A method for generating an oil/fat component by means of culturing algae, the method including: culturing marine algae belonging to *Chlamydomonas* in a culture medium containing sea salt.

[2] The method for generating an oil/fat component according to [1], in which the algae belonging to *Chlamydomonas* are *Chlamydomonas* sp. JSC4.

[3] The method for generating an oil/fat component according to [1] or [2], in which, the amount of nitrate in the culture containing sea salt measured using a wavelength of 220 nm is 10 mg/L or less.

[4] The method for generating an oil/fat component according to any one of [1] to [3], in which the mass % of the sea salt in the culture medium is in the range of 0.5% by mass to 5% by mass.

[5] The method for generating an oil/fat component according to any one of [1] to [4], in which the culture medium containing sea salt contains one of the group consisting of seawater, concentrated seawater, and artificial seawater.

[6] A method for producing a higher unsaturated fatty acid, the method including: hydrolyzing an oil/fat component obtained by the method for generating an oil/fat component according to any one of [1] to [5].

[7] The method for producing a higher unsaturated fatty acid according to [6], in which the higher unsaturated fatty acid is oleic acid or linolenic acid.

[8] *Chlamydomonas* sp. JSC4 which has an oil/fat component producing ability.

Advantageous Effects of Invention

According to the present invention, it is possible to provide a method for producing a useful carbon component with high efficiency using algae.

BRIEF DESCRIPTION OF DRAWINGS

FIG. 2 shows comparison of 18S rDNA sequences of closely related *Chlamydomonas* species (SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; and SEQ ID NO: 11 of the sequence table).

FIG. 3 shows comparison of 18S rDNA sequences of closely related *Chlamydomonas* species (SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; and SEQ ID NO: 11 of the sequence table).

FIG. 4 shows comparison of 18S rDNA sequences of closely related *Chlamydomonas* species (SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; and SEQ ID NO: 11 of the sequence table).

DESCRIPTION OF EMBODIMENTS

[Algae]

Figure 1:
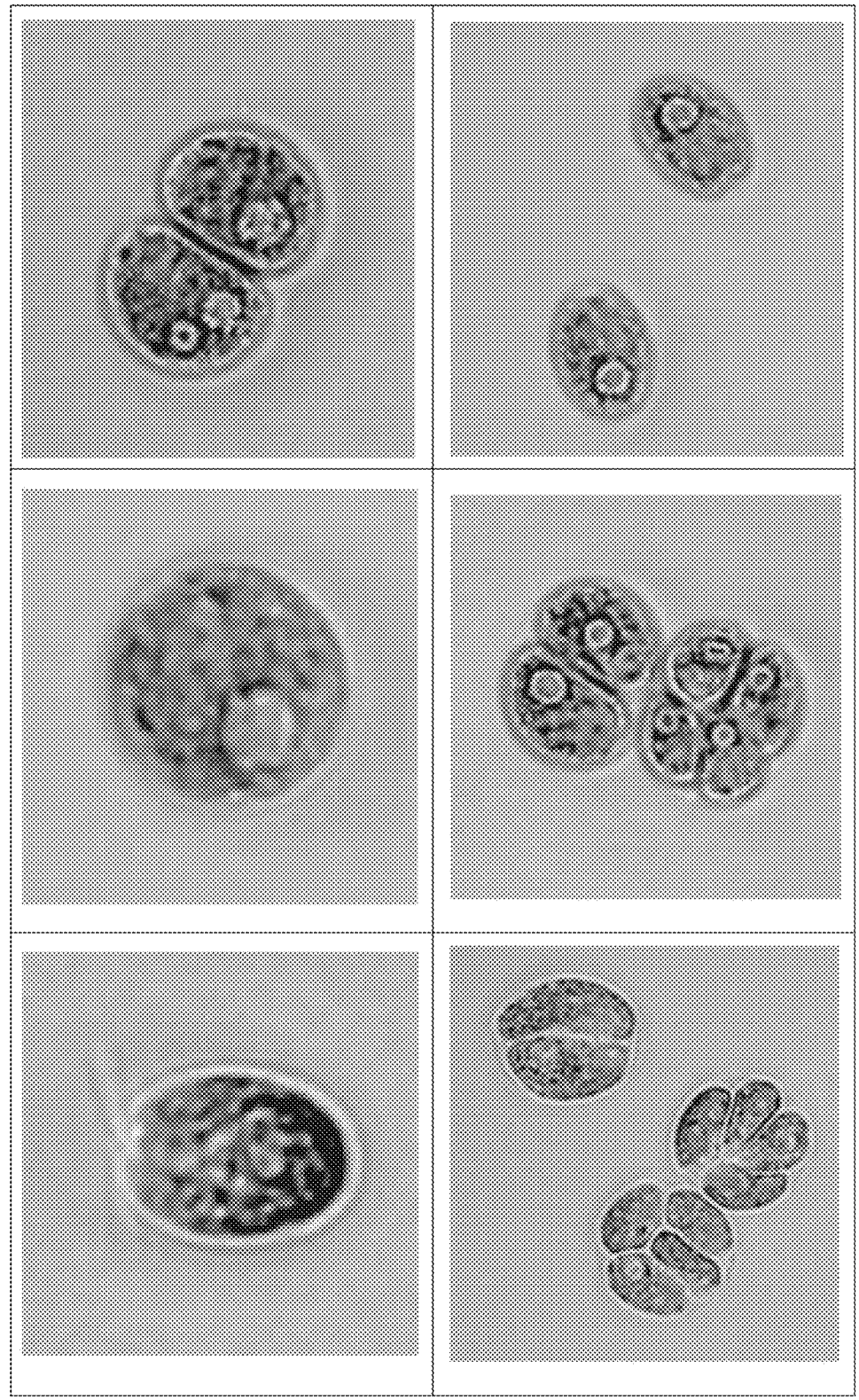
FIG. 1 is a micrograph of vegetative cells (cells which vigorously grow in a suitable growing environment and under the rich nutrient conditions) of *Chlamydomonas* sp. JSC4.

Algae used in the present invention have the characteristics of algae belonging to *Chlamydomonas*.

*Chlamydomonas* is a genus consisting of unicellular *flagellates* belonging to green algae *Chlamydomonas* (or Volvocales). *Chlamydomonas* is mostly generated in freshwater, but grown in seawater in some cases. The algae belonging to marine *Chlamydomonas* of the present invention indicate algae belonging to *Chlamydomonas*, which are generated in water or brackish water or can be grown in a culture medium containing sea salt.

The algae belonging to *Chlamydomonas* used in the present invention are not particularly limited as long as the algae are marine algae.

Since nutrient sources are present in seawater, it is not necessary to separately add nutrient sources to a culture medium. Further, it is not necessary to use pure water. Moreover, a sugar source does not need for cultivation of algae. A method for generating an oil/fat component of the present invention is excellent in cost. Moreover, since the salt concentration in a culture medium is high, there is no concern for contamination of a culture solution. The present invention is excellent simply in terms that algae belonging to *Chlamydomonas* can be cultured, mass culture is possible, and oil/fat components can be generated in a large scale.

In order to solve the above-described problem, the present inventors conducted search for algae which generate target oil/fat components with high efficiency and found that algae belonging to *Chlamydomonas* are preferable as algae.

In addition, in the *Chlamydomonas* genus, the present inventors found that *Chlamydomonas* sp. JSC4 is particularly preferable from a viewpoint of generating oil/fat components with high efficiency, thereby completing the present invention.

[*Chlamydomonas* sp. JSC4] Separation and purification of *Chlamydomonas* sp. JSC4 used in the present invention are performed by the following procedures.

That is, only one cell is isolated from brackish water samples collected from Taiwan Midwest coast and sterilized according to a conventional method. The sterilized cell is cultured under the light conditions of 20° C., 8 µmol photons/m$^2$/sec to 15 µmol photons/m$^2$/sec for 12 hours of a light period and 12 hours of a dark period using an HSM agar culture medium showing the following compositions, the algae strain is established by performing subculture once every two weeks, the algae strain is identified as green algae belonging to *Chlamydomonas* through morphological observation and the like, and the algae strain is named strain JSC4.

TABLE 1

| Compositions | mg/L |
| --- | --- |
| $NH_4Cl$ | 500 |
| $MgSO_4 \cdot 7H_2O$ | 20 |
| $CaCl_2 \cdot 2H_2O$ | 10 |
| $K_2HPO_4$ | 1,440 |
| $KH_2PO_4$ | 720 |
| $Na_2EDTA$ | 50 |
| $ZnSO_4 \cdot 7H_2O$ | 22 |
| $H_3BO_3$ | 11.4 |
| $MnCl_2 \cdot 4H_2O$ | 5.1 |
| $CoCl_2 \cdot 6H_2O$ | 1.6 |
| $CuSO_4 \cdot 5H_2O$ | 1.6 |
| $(NH_4)6Mo_7O_{24} \cdot 4H_2O$ | 1.1 |
| $FeSO_4 \cdot 7H_2O$ | 5 |
| KOH | 16 |
| Agar | 15 g |
| pH (adjust by KOH) | 7.0 |

The algological properties of *Chlamydomonas* sp. JSC4 are as follows. FIG. 1 show a micrograph of vegetative cells (cells which vigorously grow in a suitable growing environment and under the rich nutrient conditions) of *Chlamydomonas* sp. JSC4.

(Morphological Properties)

(1) The vegetative cell is oval and the size thereof is approximately 10 μm. The vegetative cell has two flagella having approximately the same size as the length of the cell. The vegetative cell has motility.

(2) The outer circumference of the vegetative cell is surrounded by a cell wall and one nucleus and one chloroplast are present in the inside thereof. In addition, mitochondria, a golgi body, a vacuole, and oil droplets are also recognized. The base of the chloroplast has a pyrenoid.

(Genital Form)

(1) Two to eight endospores are formed in a vegetative cell and equally distributed in the cell. The endospores have one nucleus and one chloroplast in the cell.

(2) Growth Through Binary Division is Carried Out.

(Physiology or Biochemical Properties)

(1) Culture solution: *Chlamydomonas* sp. JSC4 can be generated in seawater or brackish water or can be grown in a culture solution containing sea salt.

(2) Photosynthesis performance: photoautotrophic growth using photosynthesis is possible.

(3) Dyes to be contained: chlorophyll a, chlorophyll b, and other carotenoids (4) Assimilation storage material: starch (5) Growth temperature range: 15° C. to 35° C. (optimum temperature of 25° C.)

(6) Growth pH range: pH 6.0 to 10.0 (optimum pH of 7.0)

In view of the description above, *Chlamydomonas* sp. JSC4 is identified as green algae belonging to *Chlamydomonas* from the morphological observation and the like.

The base sequence of 18S rDNA genes of *Chlamydomonas* sp. JSC4 is shown in SEQ ID NO: 1 of the sequence table. FIGS. 2 to 4 show comparison of 18S rDNA sequences of closely related *Chlamydomonas* species (SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; and SEQ ID NO: 11 of the sequence table). The shading is a molecular marker sequence of *Chlamydomonas* sp. JSC4. The most closely related species of *Chlamydomonas* sp. JSC4 is *Chlamydomonas debaryana*, but *Chlamydomonas debaryana* is not the same species as *Chlamydomonas* sp. JSC4 when attention is paid to the molecular maker sequence. In this manner, *Chlamydomonas* sp. JSC4 is determined as a new microalgae strain in terms of comparison of 18S rDNA sequences.

*Chlamydomonas* sp. JSC4 is internationally deposited as the receipt number PERM ABP-22266 under the provisions of the Budapest Treaty by National Institute of Technology and Evaluation (2-5-8 Kazusa-Kamatari, Kisarazu-shi, Chiba-ken) on Mar. 5, 2014.

[Culture Medium]

In the present invention, it is preferable to use a culture medium at the time of culturing algae belonging to *Chlamydomonas*.

The culture medium to be used is not limited as long as algae belonging to *Chlamydomonas* are grown in the culture medium, but it is particularly preferable that the culture medium containing sea salt contains seawater, concentrated seawater, or artificial seawater from a viewpoint of improving oil/fat producing ability.

For example, a modified Bold 3N medium can be particularly preferably used as such a culture medium.

Examples of the culture medium other than those described above include a modified Basal medium, a modified Bristol medium, a BG-11 medium, and a modified High Salt Medium (HSM), but a modified Bold 3N medium is particularly preferable from a viewpoint of capability of generating an oil/fat component with high efficiency.

The cultivation used in the present invention is carried out, for example, under the condition in which the content of nitrogen is low.

The cultivation under the condition in which the content of nitrogen is low may be cultivation in a nitrogen-deficient state due to nitrogen consumption accompanied by the growth or cultivation carried out by transplanting the alga body in a culture medium with a low nitrogen content.

In the present invention, the content of nitrogen to be contained in a culture medium can be evaluated by measuring the content of nitrate contained in the culture medium at a wavelength of 220 nm.

The evaluation method is not limited thereto. The content of nitrogen contained in a culture medium can also be evaluated by measuring the content of nitrate or ammonium salts using an ion sensor or through absorbance measurement using a coloring reagent.

The measurement method is carried out by the method reported by Collos et al. in 1999 (Reference: Journal of Applied Phycology, Volume 11, pp. 179 to 184 (1999)).

A specific measurement method will be described in examples below.

The compositions of the modified Bold 3N medium used in the present invention are shown below.

TABLE 2

| Compositions |
|---|
| $NaNO_3$ |
| $K_2HPO_4$ |
| $MgSO_4 \cdot 7H_2O$ |
| $KH_2PO_4$ |
| NaCl |
| $CaCl_2 \cdot 2H_2O$ |
| $FeCl_3 \cdot 6H_2O$ |
| $Na_2 \cdot EDTA \cdot 2H_2O$ |
| $ZnSO_4 \cdot 7H_2O$ |
| $CoSO_4 \cdot 7H_2O$ |
| $MnSO_4 \cdot 5H_2O$ |
| $Na_2MoO_4 \cdot 2H_2O$ |
| $Na_2SeO_3$ |
| $NiCl_2 \cdot 6H_2O$ |
| Sea Salt |

[Sea Salt]

In the present invention, it is found that the concentration of sea salt in a culture medium (the mass % of the sea salt in the entire culture medium) greatly affects the oil/fat component producing ability. Accordingly, the production efficiency of oil/fat components can be improved by adding sea salt at the optimum concentration to the above-described culture medium.

Conventionally known sea salt can be exemplified as the sea salt which can be used in the present invention. The sea salt used in the present invention may be obtained by evaporating, drying, and solidifying seawater or by using seawater or a concentrated solution of seawater, but it is more preferable to use sea salt which is the solid content of seawater in order to adjust the concentration of sea salt to be contained in a culture medium.

Moreover, artificial seawater can be used. The artificial seawater used in the present invention is powder or a concentrated solution which is artificially adjusted by imitating the compositions of seawater. The artificial seawater may be replaced by natural seawater because of availability, reproducibility, and the low cost, at the time of breeding or culturing organisms for which seawater is required. Commercially available artificial seawater can be used and may become a component close to seawater by being diluted with tap water or distilled water depending on the application because the commercially available artificial seawater contains sodium chloride as a main component and various inorganic salts, a pH adjusting agent, or the like.

Further, it is possible to adjust and use salts, other than the above-described sea salt, which can be used as a culture medium suitable for the purpose of the present invention.

In the present invention, it is found that the above-described concentration of sea salt greatly affects the oil/fat producing ability.

When algae are evaluated in terms of the oil/fat producing ability (mg/L/day), the concentration of sea salt is preferably in the range of 0.5% by mass to 5% by mass and particularly preferably in the range of 2.0% by mass to 5.0% by mass from a viewpoint that the content of a target oil/fat component is high.

In addition, in a case where mass culture of algae is assumed, seawater is conveniently used, but sodium chloride can be preferably used because sodium chloride has the same effects as those of seawater with respect to generation of oils and fats.

[Culture Method]

In the present invention, algae belonging to *Chlamydomonas* can be cultured according to a conventionally known method.

In the present invention, the above-described culture medium can be used for the cultivation.

A stationary culture method can be used as the culture method used in the present invention, but a shaking culture method or a deep aeration stirring culture method is preferable as the culture method when alga body productivity of algae or oil/fat component productivity is considered. The shaking culture may be reciprocal shaking or rotary shaking. The alga body can be generated typically at a culture temperature of 15° C. to 40° C.

As described above, when the marine microalgae are cultured according to the culture method of the present invention, algae can be stably grown and *Chlamydomonas* algae with a high ratio of oil/fat components can be obtained.

Further, the light condition is not particularly limited as long as photosynthesis can be carried out, but continuous light is preferable.

After the cultivation, the recovery of the alga body from a culture solution used as a method for obtaining crude oils and fats can be performed according to a centrifugal separation method, which is a typical method, or a filtration method using filter paper or a glass filter. The alga body recovered in this manner may be used as it is or can be made into a dry alga body according to a freeze-drying method or a hot air drying method. Oil/fat components can be extracted from the obtained alga body or dry alga body.

In the present invention, it is preferable that the above-described method is performed by typically supplying carbon dioxide.

A conventionally known method can be used as the method for supplying carbon dioxide. For example, supply of carbon dioxide can be suitably performed by aerating a culture solution.

The oil/fat component generated in the present invention is triacylglyceride. Triacylglyceride is expected to be used as a bio-diesel fuel through alkyl esterification.

An ester of glycerin and a fatty acid is used as a compound exemplified as triacylglyceride in the present invention and a higher saturated or unsaturated fatty acid having 10 to 30 carbon atoms is used as a fatty acid.

Moreover, the present invention is to provide a method for producing a higher unsaturated fatty acid useful as a bio-diesel fuel.

That is, a higher unsaturated fatty acid with high combustion efficiency can be produced by hydrolyzing the oil/fat component obtained in the method of the present invention.

Examples of the higher unsaturated fatty acid with high combustion efficiency include oleic acid and linoleic acid. Between them, oleic acid is particularly preferable from a viewpoint of particularly high combustion efficiency.

As a result of examination of the optimum concentration of sea salt for generating the above-described higher unsaturated fatty acid, the concentration thereof is preferably in the range of 0.5% by mass to 5% by mass and particularly preferably in the range of 2.0% by mass to 5% by mass.

[Method for extracting oils and fats]

A typical method for extracting oils and fats can be used as the method for extracting an oil/fat component from an alga body. Particularly, a typical extraction method using an organic solvent such as a chloroform- or methanol-based solvent, which is typified by a Folch method or a Bligh-Dyer method, can be used, but the extraction method is not limited thereto.

EXAMPLES

The present invention will be described more in detail with reference to examples below, but the present invention is not limited to the examples.

(Measurement of algae concentration in culture solution) A liquid sample from a photobioreactor was filtered using a filter having a pore diameter of 0.45 μm, which was precisely weighed in advance, freeze-dried until the weight of the filtered sample became constant, and then precisely weighed. A difference in filter mass before and after the filtration was divided by the amount of the filtered liquid sample, and then the algae concentration was determined.

(Measurement of nitrogen content in culture solution) A liquid sample from a photobioreactor was filtered using a filter having a pore diameter of 0.22 μm, and diluted in 20 times with distilled water. The nitrate concentration was determined by the optical concentration at a wavelength of 220 nm ($OD_{220}$) using a UV/VIS spectrophotometer.

That is, the value at $OD_{220}$ was converted to the nitrate concentration using the calibration curve consisting of the relation between $OD_{220}$ and the nitrate content.

(Analysis of Oil/Fat Component in Alga Body)

15 mg of a freeze-dried alga body was put into a micro vial in which 0.5 g of a glass bead having a diameter of 0.5 mm was present, a 1 mL KOH solution having a concentration of 0.5 M was added thereto, and a crushing treatment was carried out using a bead beater homogenizer for 40 minutes. The treatment liquid was transferred to a 50 mL capacity heat-resistant glass bottle while being prewashed with a 7 mL KOH solution having a concentration of 0.5 M, and the bottle was tightly sealed, and then the treatment liquid was treated in a water bath at a temperature of 100° C. for 15 minutes. The resultant was cooled to room temperature, a 8 mL HCl methanol solution having a concentration of 0.7 M and 10 mL of a 14% (v/v) boron trifluoride methanol solution (manufactured by Sigma-Aldrich Co. LCC.) were added thereto, and the solution was treated in the water bath again at 100° C. for 15 minutes. After the solution was cooled to room temperature, 4 mL of a saturated salt solution and 3 mL of n-hexane were added thereto, and the solution was stirred by a vortex mixer for 5 minutes. The stirred solution was transferred to a 50 mL capacity plastic centrifuge tube and centrifuged at 7,000 rpm for 2 minutes. 100 μL of a supernatant was put into an Eppendorf tube, 890 μL of n-hexane and 10 pt of an internal standard substance (methyl pentadecanic acid, Sigma-Aldrich Co. LCC.) were added thereto, and the supernatant was centrifuged at 10,000 rpm for 3 minutes and then analyzed by a GCMS analyzer.

A DB-23 capillary column (0.25 mmϕ×60 m, film thickness of 0.15 μm, Agilent Technologies, Japan, Ltd.) was installed on the GCMS analyzer (GCMS-QP2010 Plus, Shimadzu Corporation) and 2.3 mL of helium gas was allowed to flow therein every minute. The temperatures of an injector, ion source, and interface were respectively set as 230° C., 230° C., and 250° C. Further, the column temperature was held at 50° C. for 1 minute after sample injection, increased to 175° C. by being increased 25° C. every minute, further increased to 230° C. by being increased 4° C. every minute, and then held for 5 minutes. 1 pt of the above-described supernatant was injected into the column, the column was separated at a split ratio of 5:1, each component of fatty acid methyl ester was detected in a full-scan mode of 50 m/z to 500 m/z and quantified based on the additive amount of the internal standard, and then the quantified result was set as the amount of oils and fats.

(Analysis of $CO_2$ Fixation Ability)

The growth rate with respect to the time plot based on the weight of a dry alga body was calculated using a time course profile of the biomass concentration (g/L).

The biomass production rate ($P_{biomass}$; mg/L/d) can be acquired by the following equation.

$$P_{biomass} = \Delta X/\Delta t$$

In the equation, $\Delta X$ represents the amount of change in the biomass concentration (mg/L) in the culture time $\Delta t(d)$.

Further, the $CO_2$ fixation rate ($P_{CO2}$; mg/L/d) can be acquired by the following equation.

$$P_{CO2}(mg/L/d) = 1.88 \times P_{biomass}$$

As a typical molecular formula of the biomass of algae, $CO_{0.48}H_{1.83}N_{0.11}P_{0.01}$ was used.

The $CO_2$ fixation rate (%) can be acquired by the following equation.

$$CO_2 \text{ fixation rate } (\%) = 100 \times (C_{CO2,influent} - C_{CO2,effluent})/C_{CO2,influent}$$

In the equation, $C_{CO2,influent}$ and $C_{CO2,effluent}$ respectively represent the influent concentration and the effluent concentration of $CO_2$.

Example 1

(Medium Comparison)

Respectively 1 L of the modified Basal medium, modified Bristol medium, BG-11 medium, modified Bold 3N medium, and modified High Salt Medium (HSM) whose compositions were listed in Table 3 were prepared, added to photobioreactors having a capacity of 1 L, and autoclave-sterilized. *Chlamydomonas* sp. JSC4 was cultured for 5.7 days under the conditions in which *Chlamydomonas* sp. JSC4 was inoculated to the respective photobioreactors such that the algae concentration became approximately 100 mg/L, the photobioreactors were continuously irradiated with fluorescent light having an intensity of 200 μmol photons/m²/sec at room temperature for 24 hours, 50 mL of 2% carbon dioxide-containing air was aerated every minute, and the photobioreactors were stirred using a stirrer at 200 rpm.

The analysis results of oil/fat components of each culture solution are listed in Table 4. The oil/fat content in an alga body and the lipid productivity per culture solution of the modified Bold 3N medium were the highest.

TABLE 3

| Culture medium (mg L$^{-1}$) | Modified Basal | Modified Bristol | BG-11 | Modified Bold 3N | Modified HSM |
|---|---|---|---|---|---|
| NaNO$_3$ | | 375 | 375 | 375 | |
| KNO$_3$ | 420 | | | | |
| NH$_4$Cl | | | | | 250 |
| K$_2$HPO$_4$ | 1440 | 75 | 30 | 38.3 | 1440 |
| MgSO4•7H$_2$0 | 1000 | 75 | 75 | 75 | 20 |
| KH$_2$PO$_4$ | | 175 | | 88 | 740 |
| NaCl | | 25 | | 25 | |
| Citric acid anhydrous | | | 6 | | |
| Na$_2$CO$_3$ | | | 20 | | |
| CaCl$_2$•2H$_2$0 | 110.6 | 25 | 36 | 25 | 10 |
| FeCl$_3$•6H$_2$0 | | 5 | | 1.77 | 0.15978 |
| FeSO$_4$•7H$_2$0 | 49.8 | | | | |
| Ferric ammonium citrate | | | 6 | | |
| Na$_2$•EDTA•2H$_2$0 | 500 | | 1 | 5.53 | 0.3 |
| ZnSO$_4$•7H$_2$0 | 88.2 | 0.287 | 0.222 | 0.073 | |
| ZnCl$_2$ | | | | | 0.00328 |
| CoSO$_4$•7H$_2$0 | | | | 0.016 | |
| Co(NO$_3$)$_2$•6H$_2$0 | 4.9 | | 0.0049 | | |
| CoCl$_2$•6H$_2$0 | | | | | 0.0026 |
| MnSO$_4$•5H$_2$0 | | 0.169 | | 0.584 | |
| MnCl$_2$•4H$_2$0 | 14.4 | | 1.81 | | 0.415 |
| Na$_2$MoO$_4$•2H$_2$0 | 11.9 | | 0.39 | 0.00148 | 0.00726 |
| (NH$_4$)$_6$Mo$_7$O$_{24}$•4H$_2$0 | | 0.00124 | | | |
| Na$_2$SeO$_3$ | | | | 0.00173 | |
| NiCl$_2$•6H$_2$0 | | | | 0.00149 | |
| H$_3$BO$_3$ | 114.2 | 0.061 | 2.86 | | 0.1855 |
| CuSO$_4$•5H$_2$0 | 15.7 | 0.0025 | 0.0079 | | |
| CuCl$_2$•2H$_2$0 | | | | | 0.000012 |
| Sea Salt | 20 g | 20 g | 20 g | 20 g | 20 g |

TABLE 4

| Culture medium | Modified Basal | Modified Bristol | BG-11 | Modified Bold 3N | Modified HSM |
|---|---|---|---|---|---|
| Oil/Fat content in alga body (%) | 24.1 | 35.7 | 36.0 | 41.1 | 34.8 |
| Lipid productivity per culture solution (mg/L/d) | 90.3 | 125.6 | 148.4 | 155.0 | 123.8 |

Example 2

(Effects of Addition of Sea Salt)

Respectively 1 L of culture medium in which the amounts of sea salt to be added to the modified Bold 3N medium whose compositions were listed in Table 3 were set as 0.5%, 2%, 3.5%, and 5% (w/v) were prepared, added to photobioreactors having a capacity of 1 L, and autoclave-sterilized. Chlamydomonas sp. JSC4 was cultured for 10 days under the conditions in which Chlamydomonas sp. JSC4 was inoculated to the respective photobioreactors such that the algae concentration became approximately 100 mg/L, the photobioreactors were continuously irradiated with fluorescent light having an intensity of 200 µmol photons/m$^2$/sec at room temperature for 24 hours, 50 mL of 2% carbon dioxide-containing air was aerated every minute, and the photobioreactors were stirred using a stirrer at 200 rpm.

In all cases, the content of nitrate in a culture solution was low along with the growth of an alga body and the content thereof became 10 mg/L or less for 1.9 days or 2.7 days. Next, the lipid content in an alga body and the lipid productivity were significantly increased. Particularly in a case where 2%, 3.5%, and 5% of sea salt were added, the lipid contents of in an alga body reached a high value of 50% or greater and the maximum lipid productivity was 140 mg/L/d or greater, which was extremely high.

TABLE 5

| | Amount of Sea Salt to be added | | | |
|---|---|---|---|---|
| | 0.5% | 2% | 3.5% | 5% |
| Culture day on which content of nitrate in culture solution became 10 mg/L or less | 1.9 days | 1.9 days | 2.7 days | 2.7 days |
| Lipid content in alga body at which content of nitrate in culture solution became 10 mg/L or less (%) | 15.6 | 15.8 | 15.3 | 14.5 |
| Lipid productivity per culture solution at which content of nitrate in culture solution became 10 mg/L or less (mg/L/d) | 108.9 | 110.7 | 78.9 | 55.9 |
| Culture day on which lipid productivity per culture solution became maximum | 5.7 days | 5.7 days | 6.0 days | 6.0 days |
| Lipid productivity per culture solution during 3 days from which content of nitrate in culture solution because 10 mg/L or less (mg/L/d) | 116.3 | 158.9 | 142.6 | 148.7 |
| Lipid content in alga body on tenth day of cultivation | 38.7 | 53.5 | 55.1 | 64.0 |

Example 3

(Effects of Cultivation Under Nitrogen-Deficient Condition on Quality of Biodiesel)

The quality of biodiesel is evaluated by the ratio of unsaturated fatty acids to saturated fatty acids. The content of the saturated fatty acids in biodiesel affects oxidation suppression at a high temperature. Meanwhile, the amount of the unsaturated fatty acids affects the fluidity at a low temperature. The amount of the saturated fatty acids in the biodiesel being the same as the amount of the unsaturated fatty acids in the biodiesel is important for the purpose of providing excellent characteristics at a low temperature and a high temperature for the biodiesel. The profile of fatty acids affects environmental stress caused by the nutrients in a culture medium, the outside temperature, and the light intensity. Among these, the nitrogen-deficient condition is the most important factor that affects the fat metabolism of algae.

Figures 5, 6:
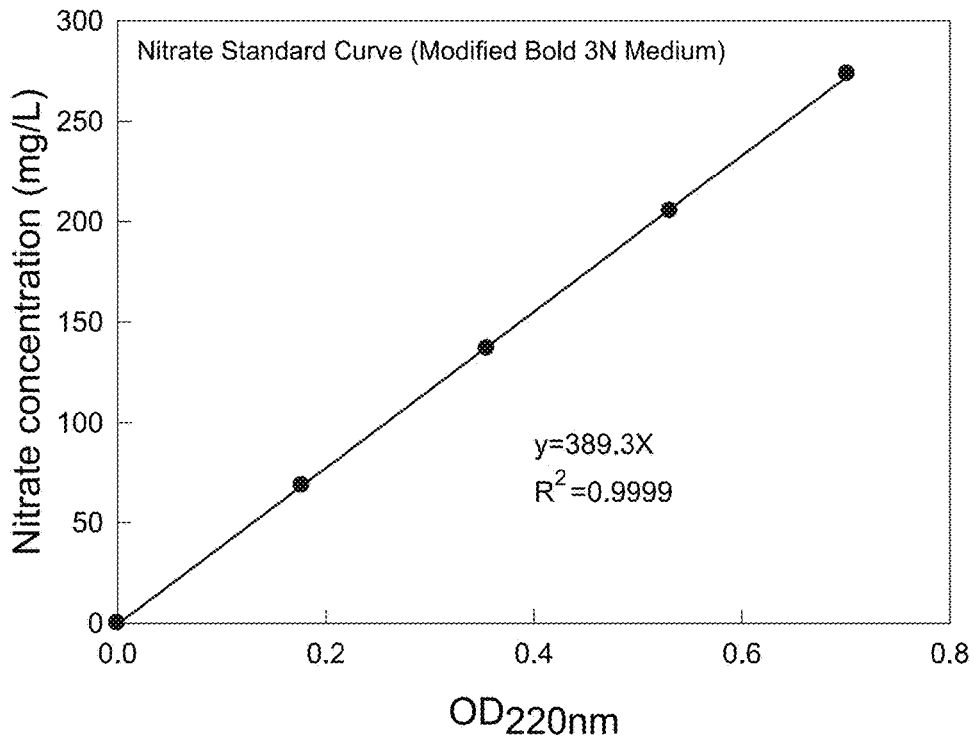
FIG. 5 is a calibration curve showing the relation between $OD_{220nm}$ and the nitrate concentration.
FIG. 6 shows results of analyzing compositions of fatty acids of *Chlamydomonas* sp. JSC4 cultured under the nitrogen-rich conditions and the nitrogen-deficient conditions.
Figure 7:
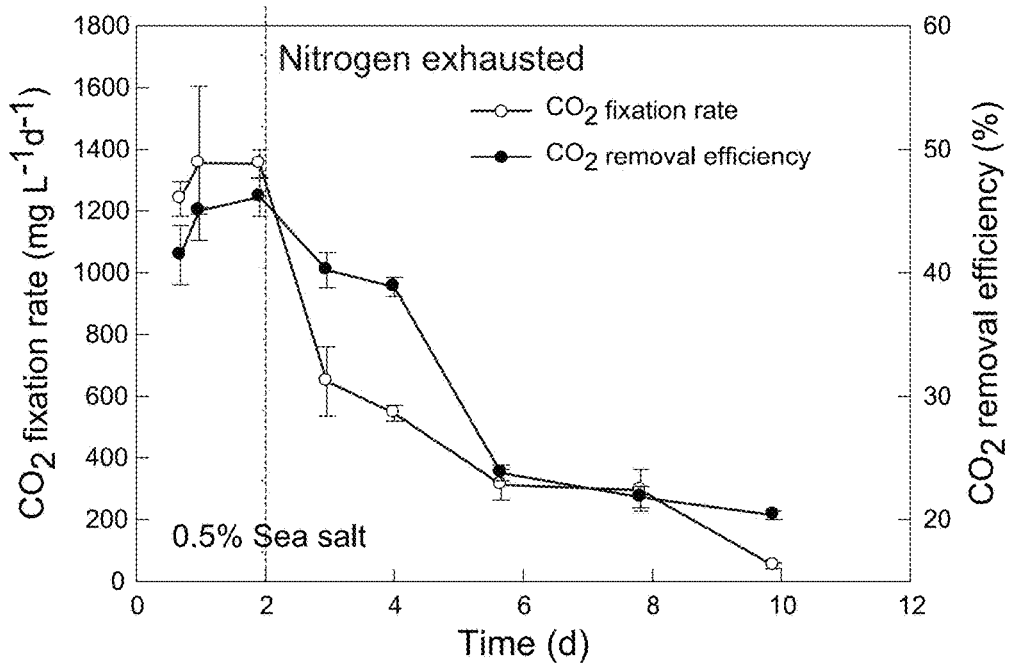
FIG. 7 shows results of analyzing $CO_2$ fixation ability of *Chlamydomonas* sp. JSC4 cultured at different seawater concentrations.
Figure 8:
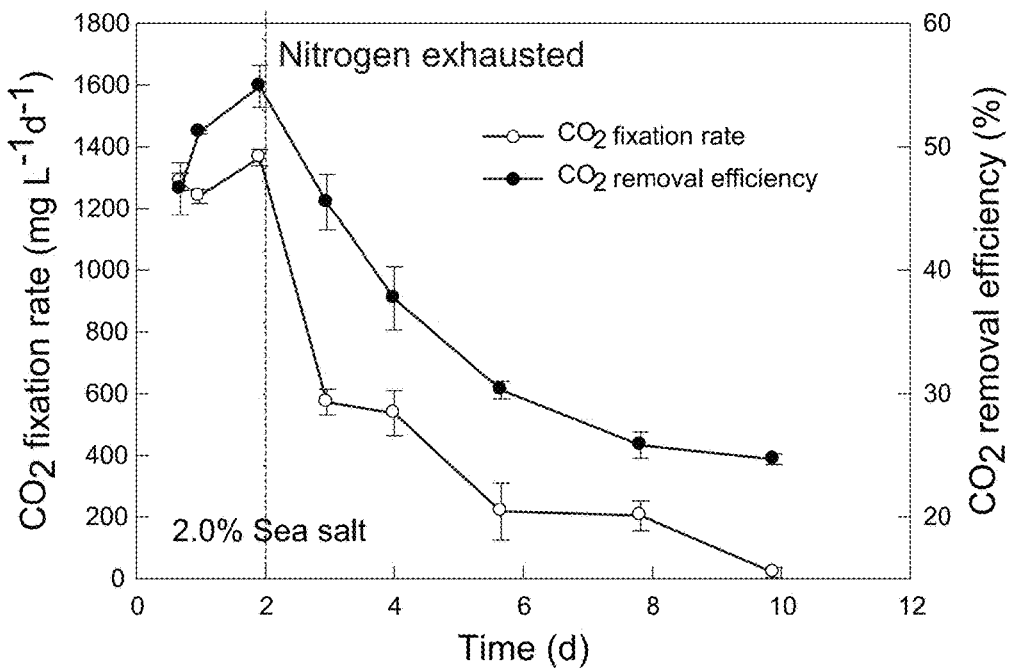
FIG. 8 shows results of analyzing $CO_2$ fixation ability of *Chlamydomonas* sp. JSC4 cultured at different seawater concentrations.
Figure 9:
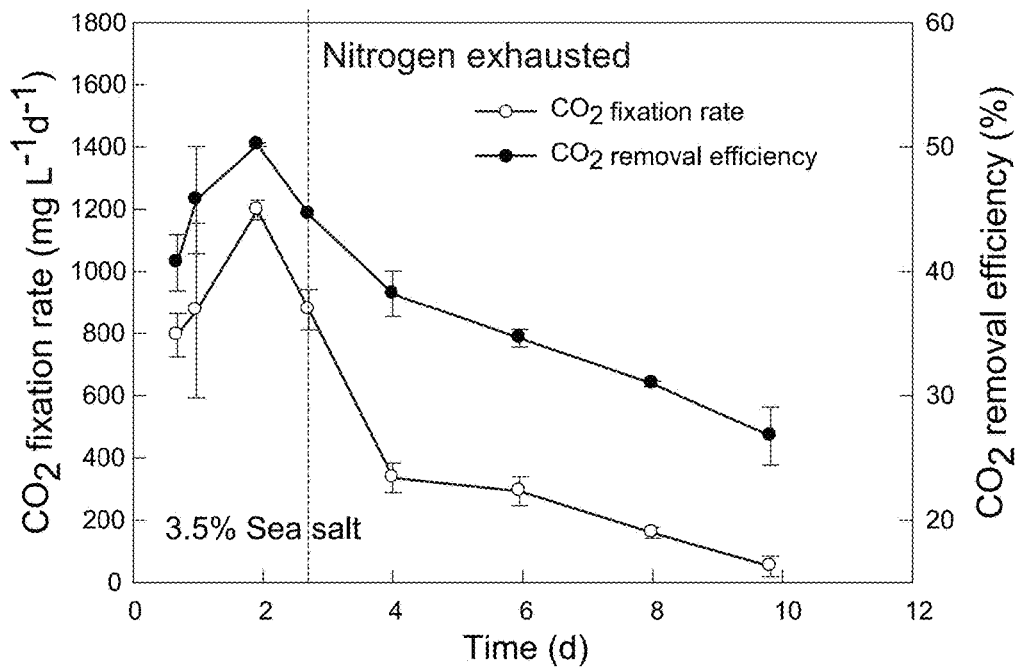
FIG. 9 shows results of analyzing $CO_2$ fixation ability of *Chlamydomonas* sp. JSC4 cultured at different seawater concentrations.
Figure 10:
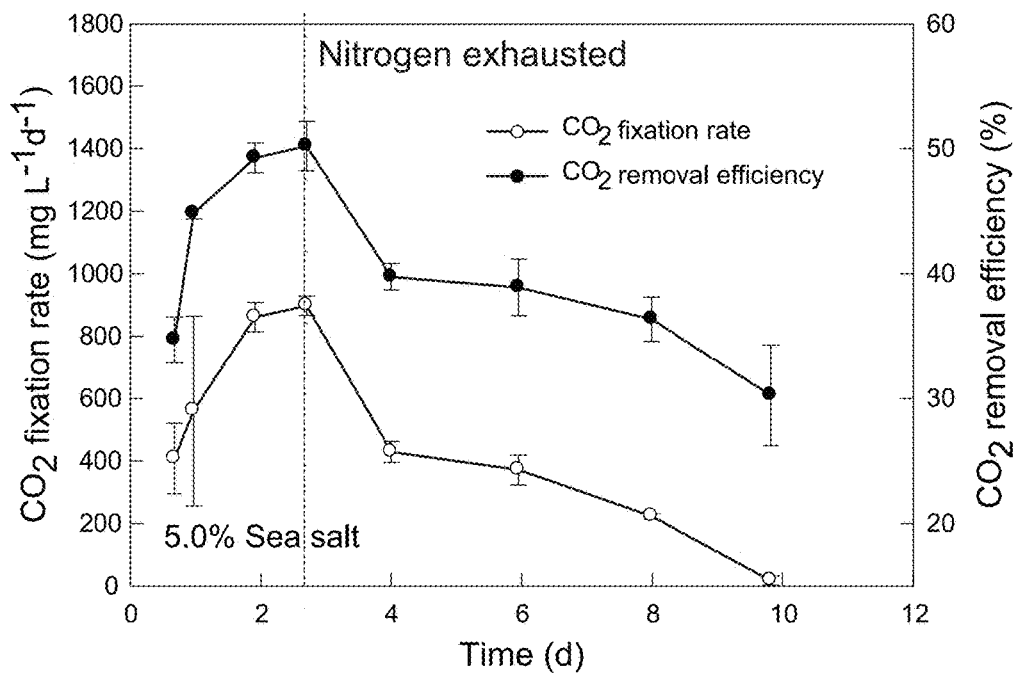
FIG. 10 shows results of analyzing $CO_2$ fixation ability of *Chlamydomonas* sp. JSC4 cultured at different seawater concentrations.

FIG. 6 shows the compositions of fatty acids of Chlamydomonas sp. JSC4 cultured under the nitrogen-rich conditions and the nitrogen-deficient conditions. In FIG. 6, as a control, the compositions of fatty acids are compared to the compositions of fatty acids derived from soybean oil. The culture conditions of Chlamydomonas sp. JSC4 are the same as those in Example 2.

As shown in FIG. 6, in regard to accumulation of oils and fats in Chlamydomonas sp. JSC4 under the nitrogen-deficient conditions, it was confirmed that oleic acid (C18:1) was likely to be increased and linolenic acid (C18:3) was likely to be decreased. According to the characteristics of biodiesel, when oleic acid is contained at a high ratio, biodiesel has more excellent oxidation stability and suitable clogging points (CFPP) at a low outside temperature. Moreover, the upper limit of the content of linolenic acid (C18:3) is set to 12% (m/m) based on the European biofuel standard (EN14214). Accordingly, it was confirmed that oils and fats produced by Chlamydomonas sp. JSC4 has the quality suitable for producing biofuels.

Further, as shown in FIG. 6, compared to the compositions of fatty acids derived from soybean oil, the content of saturated fatty acids was high and the content of polyvalent unsaturated fatty acids (n 2) was low in Chlamydomonas sp. JSC4. Typically, the high content of saturated fatty acids in oils and fats leads to excellent fluidity and density for biofuels. Meanwhile, the low content of polyvalent unsaturated fatty acids leads to improvement of oxidation stability at a low outside temperature and provision of suitable clogging points. Therefore, from the viewpoint that Chlamydomonas sp. JSC4 has a profile of fatty acids suitable for oils and fats, it was confirmed that Chlamydomonas sp. JSC4 is a strain suitable for production of biofuels.

Example 4

(Effects of Controlling Sea Salt and Nitrogen Source on $CO_2$ Fixation of Chlamydomonas sp. JSC4)

The $CO_2$ fixation ability of Chlamydomonas sp. JSC4 that was cultured at culture media whose contents of sea salt were different from each other was examined at constant time intervals. The results thereof are shown in FIGS. 7 to 10. As shown in FIGS. 7 to 10, the $CO_2$ fixation rate and the $CO_2$ fixed-speed at different concentrations of sea salt show the same tendency over the elapsed time. In other words, gradually decreasing bell type curves were shown after reaching the maximum values from 2 to 3 days of cultivation.

In FIGS. 7 to 10, the maximum values of the $CO_2$ fixation rate and the $CO_2$ fixed-speed were obtained under the condition in which the amount of sea salt to be added was 2% and the values were respectively 54.9% and 1319.0 mg/L/d. From this excellent $CO_2$ fixation ability, it was confirmed that Chlamydomonas sp. JSC4 is a strain which can be practically applied to $CO_2$ fixation using industrial gas.

The respective configurations and combinations thereof in the above-described respective embodiments are merely examples, and additions, omissions, substitutions, and other modifications of the configurations are possible within the range not departing from the scope of the present invention. Further, the present invention is not limited by the respective embodiments, but only by the appended claims.

INDUSTRIAL APPLICABILITY

According to the present invention, useful carbon components using algae can be generated with high efficiency.

What is claimed is:

1. A method for generating an oil or fat from an algae comprising:
   culturing marine algae, *Chlamydomonas* sp. JSC4, in a culture medium containing sea salt; and
   extracting the oil or fat from the algae after the culturing step.

2. The method for generating an oil or fat according to claim 1, wherein an amount of nitrate in the culture containing sea salt is 10 mg/L or less, and wherein the amount of nitrate in the culture containing sea salt is measured using a wavelength of 220 nm using a UV/VIS spectrophotometer.

3. The method for generating an oil/fat component oil or fat according to claim 1, wherein a mass percent of the sea salt in the culture medium is in the range of 0.5% by mass to 5% by mass.

4. The method for generating an oil/fat component oil or fat according to claim 1, wherein the culture medium comprises seawater, concentrated seawater, or artificial seawater.

5. A method for producing a higher unsaturated fatty acid, the method comprising:
   hydrolyzing the oil or fat obtained by the method of claim 1.

6. The method for producing a higher unsaturated fatty acid according to claim 5, wherein the higher unsaturated fatty acid is oleic acid or linolenic acid.

7. *Chlamydomonas* sp. JSC4A (FERM BP-22266) which has an oil or fact producing ability.

8. The method for generating an oil or fat according to claim 2, wherein a mass percent of the sea salt in the culture medium is in the range of 0.5% by mass to 5% by mass.

9. The method for generating an oil or fat according to claim 1, wherein the culture medium containing sea salt contains one of the group consisting of seawater, concentrated seawater, and artificial seawater.

10. The method for generating an oil or fat according to claim 2, wherein the culture medium containing sea salt contains one of the group consisting of seawater, concentrated seawater, and artificial seawater.

11. The method for generating an oil or fat according to claim 3, wherein the culture medium containing sea salt contains one of the group consisting of seawater, concentrated seawater, and artificial seawater.

12. A method for producing a higher unsaturated fatty acid, the method comprising:
   hydrolyzing the oil or fat obtained by the method of claim 2.

13. A method for producing a higher unsaturated fatty acid, the method comprising:
   hydrolyzing the oil or fat obtained by the method of claim 3.

14. A method for producing a higher unsaturated fatty acid, the method comprising:
   hydrolyzing the oil or fat obtained by the method of claim 4.

* * * * *

SEQUENCE LISTING

```
<160> NUMBER OF SEQ ID NOS: 11

<210> SEQ ID NO 1
<211> LENGTH: 495
<212> TYPE: DNA
<213> ORGANISM: Chlamydomonas sp. JSC4

<400> SEQUENCE: 1
tacttagcat ggaataacac gataggactc tggcctatct gttggtctgt gggaccggag      60
taatgattaa gaggggtagg cggggcatt cgtatcccgt tgtcagaggt gagattcttg     120
gatgtacgga agacaaacat ctgcgaaagc atttgccaag gatactttca ttgatcaagg    180 ggttggggc ttgaagacgg ttagataccg tcgtagtctc aaccataaac gatgccgact    240
agggattggc agatgttcct ttgatgactc tgccagcacc ttataaggaa tcaaagtttt    300
tgggttccgg ggggagtatg gtcacaacgc tgaaacttga aggaattgac ggaagggcac    360
caccagggcc acaagcctgc ggcttaattt gtctcaacac ggggaaactt accaggtcca    420
gacacgggaa ggattgacag attgagagct ctttcttaat tctgtgggtc gtggtgcatg    480
gccgttctta gttgg                                                     495

<210> SEQ ID NO 2
<211> LENGTH: 500
<212> TYPE: DNA
<213> ORGANISM: Chlamydomonas debaryana
<220> FEATURE:
<221> NAME/KEY: misc_feature
<222> LOCATION: (142)..(142)
<223> OTHER INFORMATION: n is a, c, g, or t

<400> SEQUENCE: 2
tacattagca tggaataaca cgataggact ctggcctatc tgttggtctg tgggaccgga      60
gtaatgatta agaggggtag tcgggggcat tcgtattccg ttgtcagagg tgaaattcct    120
ggatttacgg aagacgaaca tntgcgaaag catttgccaa ggatactttc attgatcaag    180
aacgaaagtt gggggctcga agacgattag ataccgtcgt agtctcaacc ataaacgatg    240
ccgactaggg attggcagat gttcctttga tgactctgcc agcaccttat gagaaatcaa    300 agttttggg ttccgggggg agtatggtcg caaggctgaa acttaaagga attgacggaa    360
gggcaccacc aggcgtggag cctgcggctt aatttgactc aacacgggga aacttaccag    420
gtccagacac gggaaggatt gacagattga gagctctttc ttgattctgt gggtggtggt    480
gcatggccgt tcttagttgg                                                500

<210> SEQ ID NO 3
<211> LENGTH: 500
<212> TYPE: DNA
<213> ORGANISM: Chlamydomonas cribrum

<400> SEQUENCE: 3
tacattagca tggaataaca cgataggact ctggcctatc tgttggtctg tgggaccgga      60
gtaatgatta agaggggtag tcgggggcat tcgtattgcg ttgtcagagg tgaaattcct    120
ggatttacgc aagacgaaca tctgcgaaag catttgccaa ggatactttc attgatcaag    180
```

| | |
|---|---|
| aacgaaagtt gggggctcga agacgattag ataccgtcgt agtctcaacc ataaacgatg | 240 |
| ccgactaggg attggcgggt gttcctttga tgaccccgcc agcaccttat gagaaatcaa | 300 |
| agtttttggg ttccgggggg agtatggtcg caaggctgaa acttaaagga attgacggaa | 360 |
| gggcaccacc aggcgtggag cctgcggctt aatttgactc aacacgggga agcttaccag | 420 |
| gtccagacac gggaaggact gacagattga gagctctttc ttgattctgt gggtggtggt | 480 |
| gcatggccgt tcttagttgg | 500 |

<210> SEQ ID NO 4
<211> LENGTH: 500
<212> TYPE: DNA
<213> ORGANISM: Chlamydomonas incerta

<400> SEQUENCE: 4

| | |
|---|---|
| tacattagca tggaataaca cgataggact ctggcctatc tgttggtctg tgggaccgga | 60 |
| gtaatgatta agaggggtag tcgggggcat tcgtattccg ttgtcagagg tgaaattctt | 120 |
| ggatttacgg aagacgaaca tctgcgaaag catttgccaa ggatactttc attgatcaag | 180 |
| aacgaaagtt gggggctcga agacgattag ataccgtcgt agtctcaacc ataaacgatg | 240 |
| ccgactaggg attggcagat gttcttttga tgactctgcc agcaccttat gagaaatcaa | 300 |
| agtttttggg ttccgggggg agtatggtcg caaggctgaa acttaaagga attgacggaa | 360 |
| gggcaccacc aggcgtggag cctgcggctt aatttgactc aacacgggga aacttaccag | 420 |
| gtccagacac gggaaggatt gacagattga gagctctttc ttgattctgt gggtggtggt | 480 |
| gcatggccgt tcttagttgg | 500 |

<210> SEQ ID NO 5
<211> LENGTH: 500
<212> TYPE: DNA
<213> ORGANISM: Chlamydomonas reinhardtii

<400> SEQUENCE: 5

| | |
|---|---|
| tacattagca tggaataaca cgataggact ctggcctatc tgttggtctg tgggaccgga | 60 |
| gtaatgatta agaggggtag tcgggggcat tcgtattccg ttgtcagagg tgaaattctt | 120 |
| ggatttacgg aagacgaaca tctgcgaaag catttgccaa ggatactttc attgatcaag | 180 |
| aacgaaagtt gggggctcga agacgattag ataccgtcgt agtctcaacc ataaacgatg | 240 |
| ccgactaggg attggcagat gttcttttga tgactctgcc agcaccttat gagaaatcaa | 300 |
| agtttttggg ttccgggggg agtatggtcg caaggctgaa acttaaagga attgacggaa | 360 |
| gggcaccacc aggcgtggag cctgcggctt aatttgactc aacacgggga aacttaccag | 420 |
| gtccagacac gggaaggatt gacagattga gagctctttc ttgattctgt gggtggtggt | 480 |
| gcatggccgt tcttagttgg | 500 |

<210> SEQ ID NO 6
<211> LENGTH: 500
<212> TYPE: DNA
<213> ORGANISM: Chlamydomonas zebra

<400> SEQUENCE: 6

| | |
|---|---|
| tacattagca tggaataaca cgataggact ctggcctatc tgttggtctg tgggactgga | 60 |
| gtaatgatta agaggggtag tcgggggcat tcgtattccg ttgtcagagg tgaaattctt | 120 |
| ggatttacgg aagacgaaca tctgcgaaag catttgccaa ggatactttc attgatcaag | 180 |
| aacgaaagtt gggggctcga agacgattag ataccgtcgt agtctcaacc ataaacgatg | 240 |

-continued

```
ccgactaggg attggcggat gttcttttga tgactccgcc agcaccttat gagaaatcaa      300 agttttggg ttccggggg agtatggtcg caaggctgaa acttaaagga attgacggaa       360
gggcaccacc aggcgtggag cctgcggctt aatttgactc aacacgggga aacttaccag      420
gtccagacac gggaaggatt gacagattga gagctctttc ttgattctgt gggtggtggt      480
gcatggccgt tcttagttgg                                                  500
```

<210> SEQ ID NO 7
<211> LENGTH: 500
<212> TYPE: DNA
<213> ORGANISM: Chlamydomonas oogama
<220> FEATURE:
<221> NAME/KEY: misc_feature
<222> LOCATION: (150)..(150)
<223> OTHER INFORMATION: n is a, c, g, or t

<400> SEQUENCE: 7

```
tacattagca tggaataaca cgataggact ctggcctatc tgttggtctg tgggaccgga       60
gtaatgatta agagggtag tcgggggcat tcgtattccg ttgtcagagg tgaaattctt      120
ggatttacgg aagacgaaca tctgcgaaan catttgccaa ggatactttc attgatcaag      180
aacgaaagtt gggggctcga agacgattag ataccgtcgt agtctcaacc ataaacgatg      240
ccgactaggg attggcagat gttcctttaa tgactctgcc agcaccttat gagaaatcaa      300 agttttggg ttccggggg agtatggtcg caaggctgaa acttaaagga attgacggaa       360
gggcaccacc aggcgtggag cctgcggctt aatttgactc aacacgggga aacttaccag      420
gtccagacac gggaaggatt gacagattga gagctctttc ttgattctgt gggtggtggt      480
gcatggccgt tcttagttgg                                                  500
```

<210> SEQ ID NO 8
<211> LENGTH: 501
<212> TYPE: DNA
<213> ORGANISM: Chlamydomonas longispicula

<400> SEQUENCE: 8

```
tacgttagca tggaataaca tgataggact ctggcctatc ttgttggtct gtaggactgg       60
agtaatgatt aagagggaca gtcgggggca ttcgtattgc gctgtcagag gtgaaattct      120
tggatttgcg caagacgaac atctgcgaaa gcatttgcca aggatgtttt cattgatcaa      180
gaacgaaagt tgggggctcg aagacgatta gataccgtcg tagtctcaac cataaacgat      240
gccgactagg gattggtggg agtttcttcg atgactccgc cagcaccttta tgagaaatca      300 aagtctctgg gttccggggg gagtatggtc gcaaggctga aacttaaagg aattgacgga      360
agggcaccac caggcgtgga gcctgcggct taatttgact caacacggga aaacttacca      420
ggtccagaca cagggaggat tgacagattg agagctcttt cttgattctg tgggtggtgg      480
tgcatggccg ttcttagttg g                                                501
```

<210> SEQ ID NO 9
<211> LENGTH: 499
<212> TYPE: DNA
<213> ORGANISM: Chlamydomonas pseudovolvox

<400> SEQUENCE: 9

```
tacattagca tggaataaca cgataggact ctggcctatc tgttggtctg tgggaccgga       60
gtaatgatta agagggacag tcgggggcat tcgtattcca ttgtcagagg tgaaattctt      120
ggatttatgg aagacgaaca tctgcgaaag catttgccaa ggatgtttca ttgatcaaga      180
```

```
acgaaagttg ggggctcgaa gacgattaga taccgtcgta gtctcaacca taaacgatgc    240
cgactaggga ttggcagatg ttccattgat gactctgcca gcaccttatg agaaatcaaa    300
gtttttgggt tccgggggga gtatggtcgc aaggttgaaa cttaaaggaa ttgacggaag    360
ggcaccacca ggcgtggagc ctgcggctta atttgactca acacggggaa acttaccagg    420
tccagacacg ggaaggattg acagattgag agctctttct tgattctgtg ggtggtggtg    480
catggccgtt cttagttgg                                                 499

<210> SEQ ID NO 10
<211> LENGTH: 500
<212> TYPE: DNA
<213> ORGANISM: Chlamydomonas sociale

<400> SEQUENCE: 10
tacattagca tggaataaca tgataggact ctggcctatc tgttggtctg tgggaccgga     60
gtaatgatta agaggggtag tcgggggcat tcgtattccg ttgtcagagg tgaaattctt    120
ggatttacgg aagacgaaca tctgcgaaag catttgccaa ggatactttc attgatcaag    180
aacgaaagtt gggggctcga agacgattag ataccgtcgt agtctcaacc ataaacgatg    240
ccgactaggg attggcagat gttccttttga tgactctgcc agcaccttat gagaaatcaa    300
agttttgggg ttccgggggg agtatggtcg caaggctgaa acttaaagga attgacggaa    360
gggcaccacc aggcgtggag cctgcggctt aatttgactc aacacgggga aacttaccag    420
gtccagacac gggaaggatt gacagattga gagctctttc ttgattctgt gggtggtggt    480
gcatggccgt tcttagttgg                                                500

<210> SEQ ID NO 11
<211> LENGTH: 500
<212> TYPE: DNA
<213> ORGANISM: Chlamydomonas carteri

<400> SEQUENCE: 11
tacattagca tggaataaca cgataggact ctggcctatc tgttggtctg tgggatcgga     60
gtaatgatta agaggggtag tcgggggcat tcgtattccg ttgtcagagg tgaaattctt    120
ggatttacgg aagacgaaca tctgcgaaag catttgccaa ggatactttc attgatcaag    180
aacgaaagtt gggggctcga agacgattag ataccgtcgt agtctcaacc ataaacgatg    240
ccgactaggg attggcagat gttcttttga tgactctgcc agcaccttat gagaaatcaa    300
agttttgggg ttccgggggg agtatggtcg caaggctgaa acttaaagga attgacggaa    360
gggcaccacc aggcgtggag cctgcggctt aatttgactc aacacgggga aacttaccag    420
gtccagacac gggaaggatt gacagattga gagctctttc ttgattctgt gggtggtggt    480
gcatggccgt tcttagttgg                                                500
```